US00PP37828P2

(12) United States Plant Patent
Smit

(10) Patent No.: US PP37,828 P2
(45) Date of Patent: Oct. 27, 2026

(54) ***EUPHORBIA TITHYMALOIDES* PLANT NAMED 'EC-PEDI-2601'**

(50) Latin Name: *Euphorbia tithymaloides*
Varietal Denomination: EC-PEDI-2601

(71) Applicant: Eden Collection B.V., Sappemeer (NL)

(72) Inventor: Obed Jacob Smit, Sappemeer (NL)

( * ) Notice: Subject to any disclaimer, the term of this patent is extended or adjusted under 35 U.S.C. 154(b) by 0 days.

(21) Appl. No.: 19/571,084

(22) Filed: Mar. 18, 2026

(51) Int. Cl.
*A01H 5/12* (2018.01)
*A01H 6/38* (2018.01)

(52) U.S. Cl.
USPC ..... Plt./302

(58) Field of Classification Search
USPC ..... Plt./302
See application file for complete search history.

*Primary Examiner* — Susan McCormick Ewoldt

(57) ABSTRACT

A new and distinct cultivar of *Euphorbia* plant named 'EC-PEDI-2601' is disclosed, characterized by a unique variegated leaf pattern of light and dark green tints and shades, and stems colored white-green and growing in a distinct zig-zag pattern. The new cultivar is a *Euphorbia*, typically used for ornamental horticulture purposes.

2 Drawing Sheets

Latin name of the genus and species: *Euphorbia tithymaloides.*

Cultivar denomination: 'EC-PEDI-2601'.

BACKGROUND OF THE INVENTION

The new cultivar is the product of a naturally-occurring branch mutation of *Euphorbia tithymaloides*, the species itself. The new cultivar was discovered and selected by the inventor in May 2024, at a nursery in Sapemeer, the Netherlands.

Asexual reproduction of the new cultivar 'EC-PEDI-2601' was first performed by terminal cuttings at a nursery in Sapemeer, the Netherlands in July 2024, and has shown that the unique features of this cultivar are stable and reproduced true to type in successive generations.

SUMMARY OF THE INVENTION

The cultivar 'EC-PEDI-2601' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'EC-PEDI-2601' These characteristics in combination distinguish 'EC-PEDI-2601' as a new and distinct *Euphorbia* cultivar:

1. Unique variegated leaf pattern of light and dark green tints and shades.
2. Zigzag white-green plant stems.

PARENT COMPARISON

Plants of the new cultivar 'EC-PEDI-2601' are similar to plants of the parent in most horticultural characteristics. However, plants of the new cultivar 'EC-PEDI-2601' differ in the following:

1. Foliage of the new cultivar is variegated, while foliage of the seed parent is not variegated.

2. Stem color of the new cultivar is white-green, while the stem color of the seed parent is green.

COMMERCIAL COMPARISON

Plants of the new cultivar 'EC-PEDI-2601' are similar to plants of the commercial cultivar, *Euphorbia tithymaloides* 'Variegata', unpatented, in most horticultural characteristics, however, plants of the new cultivar 'EC-PEDI-2601' differ in the following ways:

1. 'EC-PEDI-2601' has foliage with light and dark green tints and shades; foliage of 'Variegata' is green, white and pink.
2. 'EC-PEDI-2601' is a denser plant with more branches;, 'Variegata' plants are leggier with longer internodes and less branching.
3. 'EC-PEDI-2601' has a unique zig-zag growth pattern to the stem; stems of 'Variegata' are straight or have a very subtle zig zag.

BRIEF DESCRIPTION OF THE PHOTOGRAPHS

The photographs were taken using conventional techniques and equipment. While the colors in these photographs may display variances of color as compared to the living cultivar, due to LRV (light reflectance value), they are as accurate as possible using conventional photographic techniques. Colors in the photographs may appear to differ slightly from the color values cited in the botanical description, which accurately describe the colors of new *Euphorbia* 'EC-PEDI-2601'.

DETAILED BOTANICAL DESCRIPTION

Figure 1:
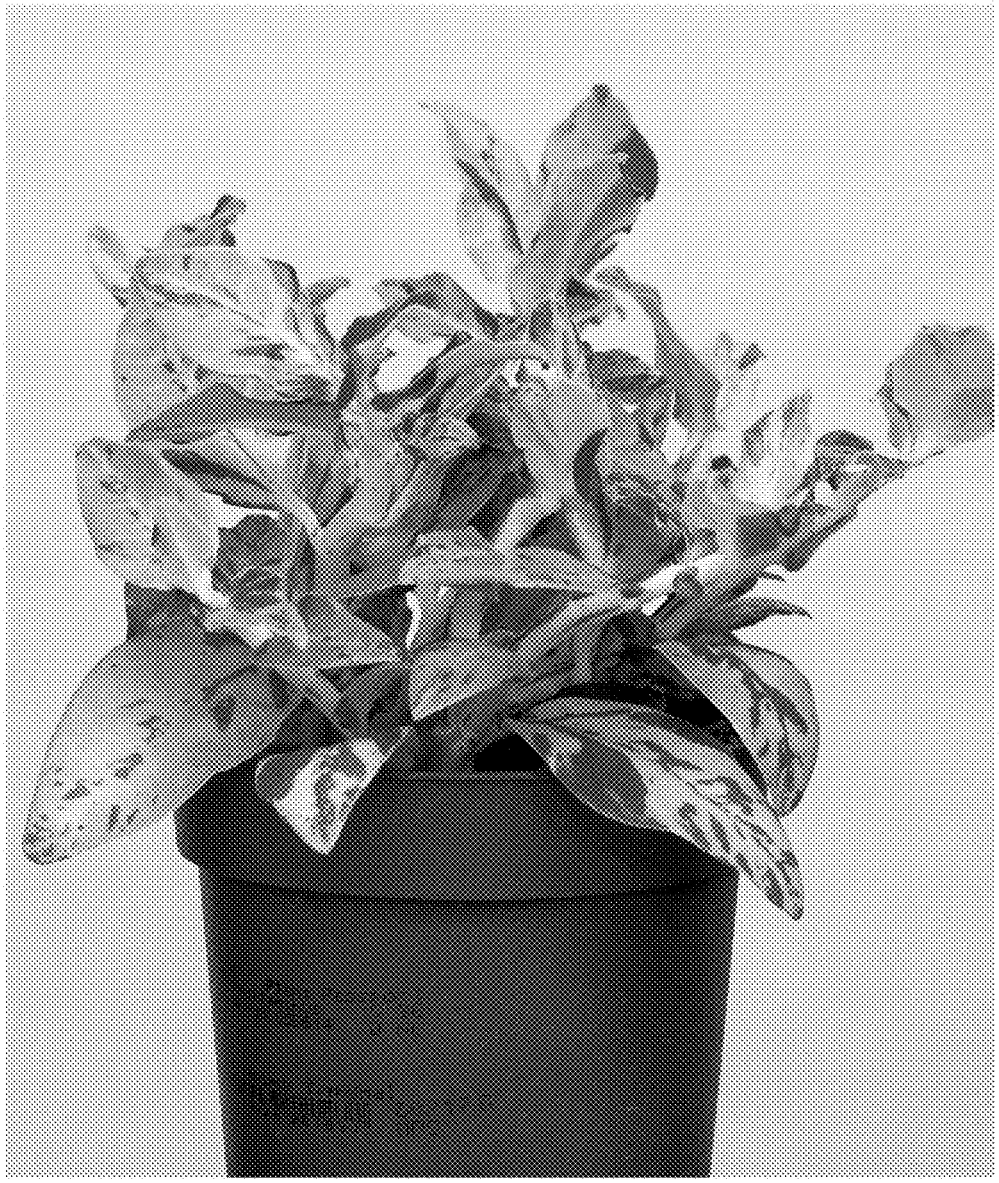
FIG. 1 illustrates in full color the plant being described of *Euphorbia* 'EC-PEDI-2601', grown in a greenhouse (approximately 3500 foot candles) in Sapemeer, the Netherlands.
Figure 2:
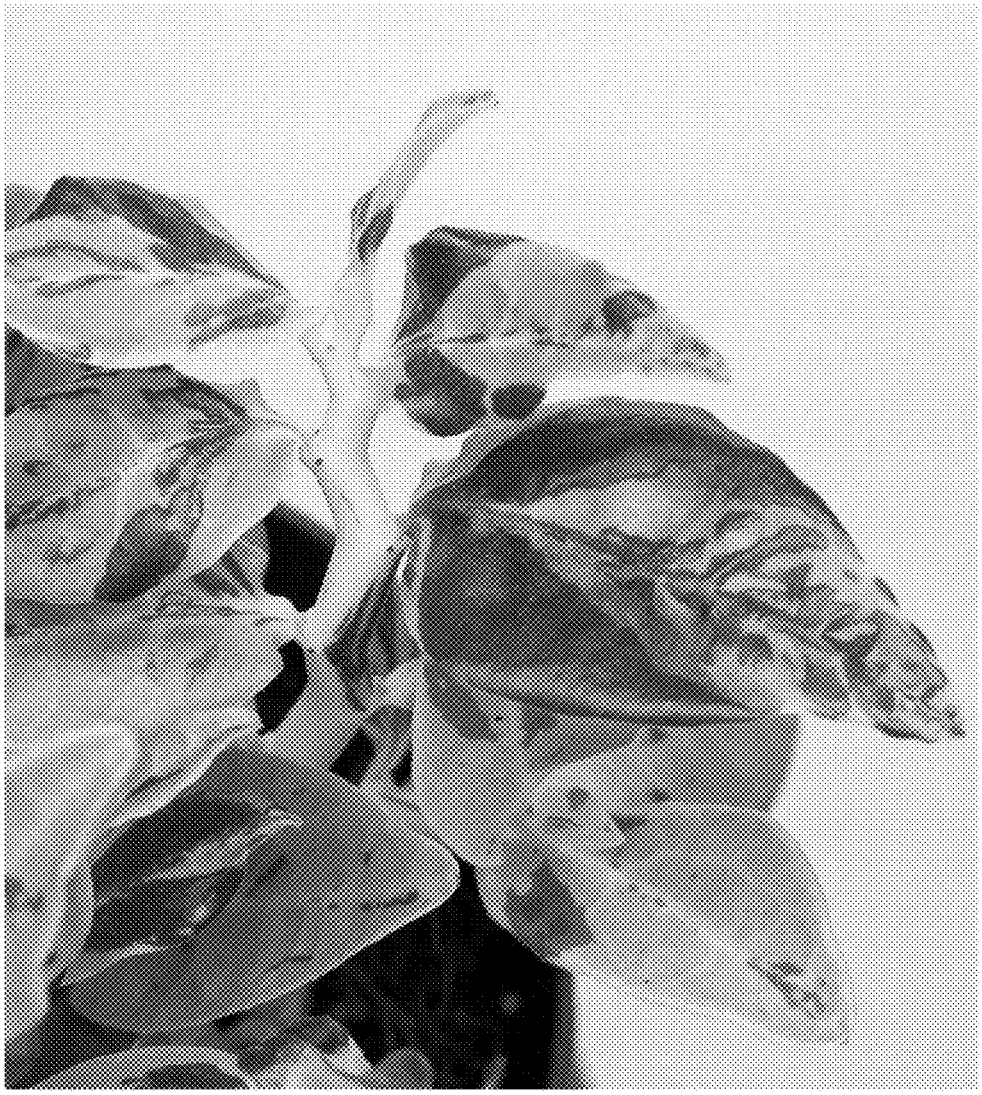
FIG. 2 illustrates in full color a close-up view of typical foliage and a stem of *Euphorbia* 'EC-PEDI-2601', grown in full sun (approximately 9500 foot candles) in Sapemeer, the Netherlands.

In the following description, color references are made to The Royal Horticultural Society Color Chart 2019, except where general terms of ordinary dictionary significance are used. The following observations and measurements describe 'EC-PEDI-2601' plants grown in a commercial greenhouse. The growing temperature ranged from approximately 19° C. to 21° C. during the day, and 17° C. to 18° C. at night. No artificial light, photoperiodic treatments or chemical treatments were given to the plants. Natural light conditions were approximately 9500 foot candles of light. Measurements and numerical values represent averages of typical plant types.

Botanical classification: *Euphorbia tithymaloides* 'EC-PEDI-2601'.

PROPAGATION

Type of propagation typically used: Top cuttings.

Time to develop roots: About 21 days at approximately 21° C. in summer; 28 days at approximately 18° C. in winter.

Root description: Moderately dense, fine, herbaceous, freely branching. White in color, not accurately measured with R.H.S. chart.

PLANT

Age of plant described: Approximately 10 weeks.

Container size of the plant described: 10 cm.

General plant description: Perennial potted plant.

Overall plant shape: Upright to spreading-upright.

Growth habit: Basal branching with lateral branches.

Plant spread: Approximately 10.4 cm.

Plant height: Approximately 11.8 cm.

Growth rate: High.

Plant vigor: High.

Branching habit: Basal branching with lateral branches.

Pinching: Yes, plants pinched 50 days before description.

Number of primary (main) branches per plant: Average 2.

Number of secondary (lateral) branches per plant: Average 1.

Branches:

- *Length*.—Average 8.9 cm.
- *Diameter*.—Average 0.5 cm.
- *Internode length*.—Average 1.1 cm.
- *Appearance and shape*.—Rounded, smooth, finely pubescent with very small hairs.
- *Luster*.—Very slightly glossy, dark patches matte.
- *Aspect/angle from vertical*.—Average angle 85°.
- *Strength*.—Moderately strong.
- *Color, developing*.—RHS Yellow-Green 150D, when maturing axillary striped Yellow Green 147A between the nodes.
- *Color, mature*.—A blend of RHS Yellow-Green 144C and N144D, axillary striped Green NN137A between the nodes.
- *Color at internodes*.—A blend of RHS Yellow-Green 144C and N144D, occasionally striped Green NN137A.
- *Pubescence*.—Branches and leaves pubescent, hairs too small to be accurately measured (shorter than 0.1 mm), colored identically to the branch, RHS Yellow-Green 150D on young stems, mature stems a blend of Yellow-Green 144C and 144D.

FOLIAGE

Leaf:

- *Leaf arrangement*.—Alternate.
- *Compound or single*.—Single.
- *Number of leaves per branch*.—Average 11.
- *Whole leaf shape*.—Ovate to broad lanceolate.
- *Whole leaf aspect*.—Flat and occasionally very slightly axillary twisted.
- *Whole leaf length*.—Average 6.8 cm.
- *Whole leaf width*.—Average 3.5 cm.
- *Leaf apex*.—Rounded, with a minute abruptly acute tip.
- *Leaf base*.—Obtuse to rounded.
- *Leaf margin*.—Coarsely undulate.
- *Leaf lobes*.—Unlobed.
- *Leaf texture, upper side*.—Glabrous, smooth, slightly leathery, dark patches moderately leathery.
- *Leaf texture, under side*.—Glabrous, smooth, very slightly leathery, dark patches slightly leathery.
- *Leaf pubescence*.—Leaf edges pubescent, both sides of leaves sparsely pubescent, hairs too small to be accurately measured (shorter than 0.1 mm), colored identically to the leaf, RHS Yellow-Green N144C on young leaves; 144A, N144D, and Green NN137A on mature stems.
- *Leaf rugosity*.—Not rugose.
- *Leaf luster, upper side*.—Very slightly glossy, dark patches moderately glossy.
- *Leaf luster, under side*.—Very slightly glossy, dark patches slightly glossy.
- *Leaf color, young, upper side*.—RHS Yellow-Green N144C, irregular strongly marbled and blotched 144A.
- *Leaf color, young, under side*.—RHS Yellow-green 145C, irregular strongly marbled and blotched Green 138C to Greyed-Green 191C.
- *Leaf color, mature, upper side*.—RHS Yellow-Green N144D, irregular strongly marbled and blotched Green NN137A.
- *Leaf color, mature, under side*.—RHS Yellow-Green 145B, irregular strongly marbled and blotched Green 138C, 137A, and Greyed-Green 191C.
- *Venation pattern*.—Pinnate.
- *Mature leaf venation color, upper side*.—Identical to leaf upper side.
- *Mature leaf venation color, under side*.—Main vein RHS Yellow-Green 144B, secondary veins identical to leaf underside.

Petiole:

- *Petiole length*.—Average 0.6 cm.
- *Petiole diameter*.—Upper side of petiole flattened, average diameter at widest (horizontal): 0.3 cm, average diameter at narrowest (vertical): 0.2 cm.
- *Petiole texture*.—Not pubescent.
- *Petiole luster*.—Both sides slightly glossy.
- *Petiole strength*.—Medium.
- *Petiole color, upper side*.—RHS Greyed-Green 193A, main vein Yellow-Green 145B and 145C.
- *Petiole color, under side*.—RHS Yellow-Green 149D.

FLOWER

Not observed to date.

REPRODUCTIVE ORGANS

Not observed to date.

OTHER CHARACTERISTICS

Fruit and seed: Not observed to date.
Disease/pest resistance: Neither resistance nor susceptibility to normal pathogens or pests of *Euphorbia* observed.
High temperature tolerance: Unknown, at least tolerant to temperatures up to 40° C.
Low temperature tolerance: Unknown, at least hardy to USDA zone 10.
USDA hardiness zones: USDA zones 10 to 12.
Tolerance to rain: Moderate.
Tolerance to wind: Moderate.

What is claimed is:

1. A new and distinct cultivar of *Euphorbia* plant named 'EC-PEDI-2601' as herein illustrated and described.

* * * * *